United States Patent [19]

Stokke et al.

[11] Patent Number: 5,633,365
[45] Date of Patent: *May 27, 1997

[54] DETECTION OF AMPLIFIED OR DELETED CHROMOSOMAL REGIONS

[75] Inventors: Trond Stokke, San Fransisco; Daniel Pinkel, Walnut Creek; Joe W. Gray, San Fransisco, all of Calif.

[73] Assignee: The Regents of the University of California, Oakland, Calif.

[*] Notice: The term of this patent shall not extend beyond the expiration date of Pat. No. 5,472,842.

[21] Appl. No.: 430,984

[22] Filed: Apr. 28, 1995

Related U.S. Application Data

[63] Continuation of Ser. No. 132,808, Oct. 6, 1993, Pat. No. 5,472,842.

[51] Int. Cl.$^6$ .............................. C07H 21/04; C12Q 1/68
[52] U.S. Cl. .......................... 536/24.31; 435/6; 435/810; 935/6; 935/8; 935/78
[58] Field of Search ........................... 435/6, 810, 172.3, 435/252.3, 320.1; 536/24.31; 935/6, 71, 8, 77, 78, 23

[56] References Cited

FOREIGN PATENT DOCUMENTS 403402  6/1991  European Pat. Off. .

OTHER PUBLICATIONS

Matthews, Jayne A., et al. (1988) "Analytical Strategies for the Use of DNA Probes", *Analytical Biochemistry*, 169:1–25.

Cremer, T., et al. (1988) "Detection of chromosome abberations in metaphase and interphase tumor cells by in situ hybridization using chromosome–specific library probes", *Human Genetics*, 80:235–246.

Lichter, P., et al. (1988) "Delineation of individual human chromosomes in metaphase and interphase cells by in situ suppression hybridization using recombinant DNA libraries", *Human Genetics*, 80:224–234.

Kallioniemi, Anne, et al. (1994) "Detection and mapping of amplified DNA sequences in breast cancer by comparative genomic hybridization", *Proc. Nat. Sci. Acad.*, 91:2156–2160.

Kallioniemi, Anne, et al. (1992) "Comparative Genomic Hybridization for Molecular Cytogenetic Analysis of Solid Tumors", *Science*, 258:818–821.

Wiegant, Joop, et al. (1991) "In situ hybridization with fluoresceinated DNA", *Nucleic Acids Research*, 19(12):3237–3241.

J. N. Lucas et al. "Translocations between two specific human chromosomes detected by three–color 'chromosome painting'" *Cytogenet Cell Genet* vol. 62 pp. 11–12 (1993).

Annika Lindblom et al. "Deletions on Chromosome 16 in Primary Familial Breast Carcinomas Are Associated with Development of Distant Metastases" *Cancer Research* vol. 53, pp. 3707–3711 Aug. 15, 1993.

Ulf S.R. Bergerheim et al. "Deletion Mapping of Chromosomes 8, 10, and 16 in Human Prostatic Carcinoma" *Genes, Chromosomes & Cancer* vol. 3, pp. 215–220 (1991).

Elisabeth Blennow et al. "Complete characterization of a large marker chromosome by reverse and forward chromosome painting" *m Genet* (1992) vol. 90, pp. 371–374. Received: 15 Jun. 1992/Revised: 6 Jul. 1992.

(List continued on next page.)

*Primary Examiner*—Carla J. Myers
*Attorney, Agent, or Firm*—Townsend and Townsend and Crew LLP

[57] ABSTRACT

The present invention relates to in situ hybridization methods for the identification of new chromosomal abnormalities associated with various diseases. In particular, it provides probes which are specific to a region of amplification in chromosome 20.

11 Claims, 3 Drawing Sheets

OTHER PUBLICATIONS

Stefan Joos et al. "Detection of amplified DNA sequences by reverse chromosome painting using genomic tumor DNA as probe" *m Genet* (1993) vol. 90, pp. 584–589. Received: 30 Oct. 1992.

Anne Kallioniemi et al. "Comparative Genomic Hybridization for Molecular Cytogenetic Analysis of Solid Tumors" *Science* vol. 258, Oct. 30, 1992 pp. 818–821.

Peter Lichter et al. "High–Resolution Mapping of Human Chromosome 11 by in Situ Hybridization with Cosmid Clones" *Science* Vol. 247 Jan. 5, 1990 pp. 64–69.

Anne Kallioniemi et al. "ERBB2 amplification in breast cancer analyzed by fluorescence in situ hybridization" *Proc. Acad. Nat. Sci.* 89:5321–5325 (1992).

Pinkel et al. "Fluorescence in situ hybridization with human chromosome–specific libraries: Detection of trisomy 21 and translocations of chromosome 4" *Proc. Acad. Nat. Sci.* 85: 9138–9142 (1988).

Stokke, et al. "Genetic characterization of 20q amplication in human breast cancer" Abstract submitted to the 43rd Annual Meeting of the American Society of Human Genetics (Appendix 2).

ATCC/NIH Repository Catalogue, 1992, pp. 113–114.

Kallioniemi et al., Proc. Natl. Academy Sciences (1992) 89: 5321–5325.

DETECTION OF AMPLIFIED OR DELETED CHROMOSOMAL REGIONS

This is a Continuation of application Ser. No. 08/132,808 filed Oct. 6, 1993 now U.S. Pat. No. 5,472,842.

BACKGROUND OF THE INVENTION

Chromosome abnormalities are often associated with genetic disorders, degenerative diseases, and cancer. particular, the deletion or multiplication of copies of whole chromosomes or chromosomal segments, and higher level amplifications of specific regions of the genome are common occurrences in cancer. See, for example Smith, et al., *Breast Cancer Res. Treat.*, 18: Suppl. 1:5–14 (1991, van de Vijer & Nusse, *Biochim. Biophys. Acta.* 1072: 33–50 (1991), Sato, et al., *Cancer. Res.*, 50: 7184–7189 (1990). In fact, the amplification and deletion of DNA sequences containing protooncogenes and tumor-suppressor genes, respectively, are frequently characteristic of tumorigenesis. Dutrillaux, et al., *Cancer Genet. Cytogenet.*, 49:203–217 (1990). Clearly the identification of amplified and deleted regions and the cloning of the genes involved is crucial both to the study of tumorigenesis and to the development of cancer diagnostics.

The detection of amplified or deleted chromosomal regions has traditionally been done by cytogenetics. Because of the complex packing of DNA into the chromosomes, resolution of cytogenetic techniques has been limited to regions larger than about 10 Mb; approximately the width of a band in Giemsa-stained chromosomes. In complex karyotypes with multiple translocations and other genetic changes, traditional cytogenetic analysis is of little utility because karyotype information is lacking or cannot be interpreted. Teyssier, J. R., *Cancer Genet. Cytogenet.*, 37: 103 (1989). Furthermore conventional cytogenetic banding analysis is time consuming, labor intensive, and frequently difficult or impossible.

More recently, cloned probes have been used to assess the amount of a given DNA sequence in a chromosome by Southern blotting. This method is effective even if the genome is heavily rearranged so as to eliminate useful karyotype information. However, Southern blotting only gives a rough estimate of the copy number of a DNA sequence, and does not give any information about the localization of that sequence within the chromosome.

Comparative genomic hybridization (CGH) is a more recent approach to identify the presence and localization of amplified/deleted sequences. See Kallioniemi, et al., *Science*, 258:818 (1992). CGH, like Southern blotting, reveals amplifications and deletions irrespective of genome rearrangement. Additionally, CGH provides a more quantitative estimate of copy number than Souther blotting, and moreover also provides information of the localization of the amplified or deleted sequence in the normal chromosome.

Generally, where detection of deletions or amplifications is limited to the loss or gain of one copy of a sequence, the resolution of prior art methods may be limited. New techniques which provide increased sensitivity, more precise localization of the affected DNA sequence, and more quantitative estimate of copy number, even in samples of mixed normal and tumor cells is particularly desirable. The present invention provides these and other benefits.

SUMMARY OF THE INVENTION

The present invention provides methods and compositions for detecting chromosome abnormalities (such as deletions and amplifications) in a preselected chromosome. The methods comprise providing a mapped library of labeled probes specific to the chromosome; contacting a chromosome sample from a patient with the library under conditions in which the probes bind selectively with target polynucleotide sequences in the sample to form hybridization complexes; detecting the hybridization complexes; and determining the copy number of each complex.

If the selected chromosome is human chromosome 20 or 17, the preferred libraries are as shown in Table 1 and Table 2, respectively. The methods are typically carried out using fluorescent in situ hybridization and the probes are labeled with digoxigenin or biotin. The probes can be used to detect the target sequences in interphase nuclei in the sample. A reference probe which binds selectively to a sequence within the centromere of the preselected chromosome can be used as a control.

Also provided are methods of detecting specific abnormalities disclosed here. In particular, methods of detecting an amplification at about position FLpter 0.85 on human chromosome 20 are disclosed. The methods comprise contacting a chromosome sample from a patient with a composition consisting essentially of one or more labeled nucleic acid probes each of which binds selectively to a target polynucleotide sequence at about position FLpter 0.85 on human chromosome 20 under conditions in which the probe forms a stable hybridization complex with the target sequence; and detecting the hybridization complex. The probes used preferably comprise polynucleotide sequences from cS20.1.0A1, cS20.10B5, cS20.10H1, or cS20.10E2.

Also provided are compositions comprising nucleic acid probes which bind selectively to a target polynucleotide sequence at about FLpter 0.85 on human chromosome 20. The probes may be labeled for use in the methods of the invention.

The invention further provides kits for the detection of an amplification at about position FLpter 0.85 on human chromosome 20. The kits comprise a compartment which contains a nucleic acid probe which binds selectively to a target polynucleotide sequence at about FLpter 0.85 on human chromosome 20. The probes preferably comprise polynucleotide sequences from cS20.10A1, cS20.10B5, cS20.10H1, and cS20.10E2. The may further comprise Texas red avidin and biotin-labeled goat anti-avidin antibodies.

Definitions

A "chromosome sample" as used herein refers to a tissue or cell sample prepared for standard in situ hybridization methods described below. The sample is prepared such that individual chromosomes remain substantially intact and typically comprises metaphase spreads or interphase nuclei prepared according to standard techniques.

As used herein a "probe" is defined as a polynucleotide (either RNA or DNA) capable of binding to a complementary target cellular genetic sequence through one or more types of chemical bonds, usually through hydrogen bond formation. It will be understood by one of skill in the art that probes will typically substantially bind target sequences lacking complete complementarity with the probe sequence depending upon the stringency of the hybridization conditions. The probes are preferably directly labelled as with isotopes or indirectly labelled such as with biotin to which a streptavidin complex may later bind. By assaying for the presence or absence of the probe, one can detect the presence or absence of the target. Probes of the invention will typically be between about 20 kb to about 60 kb, usually between about 30 and 50 kb.

A "composition consisting essentially of one or more probes each of which binds selectively to a target polynucleotide sequence " refers to a collection of one or more probes which bind substantially to the target sequence and nowhere else in the target chromosome or genome and which allow the detection of the presence or absence of the target sequence. Such a composition may contain other nucleic acids which do not materially affect the detection of the target sequence. Such additional nucleic acids include reference probes specific to a sequence in the centromere in the chromosome.

"Bind(s) substantially " refers to complementary hybridization between an oligonucleotide and a target sequence and embraces minor mismatches that can be accommodated by reducing the stringency of the hybridization media to achieve the desired detection of the target polynucleotide sequence.

"Hybridizing " refers the binding of two single stranded nucleic acids via complementary base pairing.

"Nucleic acid " refers to a deoxyribonucleotide or ribonucleotide polymer in either single- or double-stranded form, and unless otherwise limited, would encompass known analogs of natural nucleotides that can function in a similar manner as naturally occurring nucleotides.

One of skill will recognize that the precise sequence of the particular probes described herein can be modified to a certain degree to produce probes that are "substantially identical " to the disclosed probes, but retain the ability to bind substantially to the target sequences. Such modifications are specifically covered by reference to the individual probes herein. The term "substantial identity" of polynucleotide sequences means that a polynucleotide comprises a sequence that has at least 90% sequence identity, more preferably at least 95%, compared to a reference sequence using the methods described below using standard parameters.

Two nucleic acid sequences are said to be "identical " if the sequence of nucleotides in the two sequences is the same when aligned for maximum correspondence as described below. The term "complementary to " is used herein to mean that the complementary sequence is identical to all or a portion of a reference polynucleotide sequence.

Sequence comparisons between two (or more) polynucleotides are typically performed by comparing sequences of the two sequences over a "comparison window " to identify and compare local regions of sequence similarity. A "comparison window ", as used herein, refers to a segment of at least about 20 contiguous positions, usually about 50 to about 200, more usually about 100 to about 150 in which a sequence may be compared to a reference sequence of the same number of contiguous positions after the two sequences are optimally aligned.

Optimal alignment of sequences for comparison may be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci. (U.S.A.)* 85:2444 (1988), by computerized implementations of these algorithms. These references are incorporated herein by reference.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Another indication that nucleotide sequences are substantially identical is if two molecules hybridize to the same sequence under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C.

DESCRIPTION OF THE PREFERRED EMBODIMENTS

The present invention provides methods and probe libraries useful for detecting chromosome abnormalities in situ. In particular the invention provides a means of identifying the presence of multiplications or deletions in chromosomes and rapidly identifying the chromosomal regions involved in those deletions or multiplications.

Detection and Localization of Chromosomal Abnormalities

This invention is based on the use of libraries of genomic probes in in situ hybridization to interphase nuclei or metaphase spreads of chromosomes to detect and localize chromosomal abnormalities. These abnormalities can be of several types, including extra or missing individual chromosomes, extra or missing portions of a chromosome (segmental duplications or deletions), breaks, rings and chromosomal rearrangements. Chromosomal rearrangements include translocations, dicentrics, inversions, insertions, amplification and deletions.

Generally, the methods of the invention consist of two steps: 1) The creation of a mapped library of probes, and 2) The in situ hybridization of those probes to a chromosome and subsequent detection of hybridization frequency to determine relative copy number of a particular chromosomal region.

The mapped libraries of probes consist of a set of probes which when hybridized to a normal chromosome are distributed relatively uniformly across the region of interest. The region typically is one chromosome or a part of one chromosome. In certain embodiments, the library of probes can encompass the entire genome.

Each probe in the library is hybridized to the normal chromosome in a metaphase spread in situ. The physical location of the probe on the chromosome is determined by visualization of a marker, as described in detail below. Probe locations are typically expressed as the average fractional length from the p telomere (FLpter).

Once probes which hybridize to unique regions and show a relatively uniform distribution have been identified and mapped, they may be used to probe chromosomes of unknown genetic composition to determine the presence or absence of amplifications or deletions and other abnormalities. In particular, they may be used to probe interphase nuclei which is the prevalent cell stage in most tissues that are not actively dividing. Hybridization spots may be counted by regular fluorescence microscopy to give the copy number as a function of FLpter. The copy number relative to normal cells is then indicative of various chromosome abnormalities such as amplifications, deletions and the like.

Selection of a Chromosome

Typically, the probe libraries of the present invention are derived from libraries spanning an entire chromosome. Alternatively, libraries are constructed from multiple chromosomes, or from regions spanning a segment of a chromosome. Single chromosomes may be isolated by flow sorting using methods well known to those of skill in the art. Briefly, chromosomes are isolated from cells blocked in metaphase by the addition e.g., colcemid and stained with two DNA-binding fluorescent dyes. The stained chromosomes are then passed through a cell sorter and isolated using bivariate analysis of the chromosomes by size and base pair composition (see, e.g., Blennow et al., *Hum. Genet.* 90:371–374 (1992).

One of skill would recognize that the choice of a chromosome to map may be influenced by prior knowledge of the association of a particular chromosome with certain disease conditions. For example, chromosome 17 is known to harbor several disease-linked genes including p53, RARA, NF1, CMT and ERBB and there are reports suggesting the presence of a tumor suppressor gene distal to p53 (e.g. Coles, et al. *Lancet* 336: 761–763.(1990), Cropp, et al. *Proc. Natl. Acad. Sci. USA* 87: 7737–7741. (1990) and Matsumura, et al. *Cancer Res.* 52: 3474–3477 (1992)), a gene associated with early onset breast cancer at 17 q21 (Easton, et al. *Am. J. Human Genet.*, 52:678–701 (1993)) and amplification of one or more regions in breast cancer. Kallioniemi, et al. *Proc. Natl. Acad. Sci. USA* 89: 5321–5325 (1992).

Alternatively, whole genome screening techniques such as Southern blotting, and Comparative Genome Hybridization (CGH) may be used to identify chromosomes subject to frequent deletion and amplification events and thus good candidates for further study using the present invention. In particular CGH provides an effective means for screening the genome for frequent deletion or amplification events. CGH studies have indicated that sequences on chromosome 20 q are frequently amplified in both breast tumor cell lines and primary breast tumors. Abnormalities can also be identified that are suitable for prenatal screening.

In CGH, differently labeled test DNA and normal reference DNA are hybridized simultaneously to normal chromosome metaphase spreads. The hybridization is detected with two different fluorochromes. Abnormal chromosomal regions containing duplications, deletions or amplifications are detected as changes in the ratio of the two fluorochromes along the target chromosomes. For a detailed description of CGH see Kallioniemi, et al. *Science,* 258:818–821 (1992).

One of skill would recognize that a library of the present invention could be used to screen the entire genome. However because of the high resolution of the technique and the large number of probes required to screen the entire genome, CGH or other methods are preferred for an initial screening.

Production of a Probe Library

In a preferred embodiment, a selected chromosome is isolated by flow cytometry, as described above. The chromosome is then digested with restriction enzymes appropriate to give DNA sequences of at least about 20 kb and more preferably about 40 kb. Techniques of partial sequence digestion are well known in the art. See, for example Perbal, *A Practical Guide to Molecular Cloning* 2nd Ed., Wiley N.Y. (1988) incorporated herein by reference. The resulting sequences are ligated with a vector which contains a resistance marker. The vector is transfected into and propagated in the appropriate host. Exemplary vectors suitable for this purpose include cosmids, yeast artificial chromosomes (YACs), bacterial artificial chromosomes (BACs) and P1 phage. Typically, cosmid libraries are prepared. The cosmid library then consists of single clones of the transfected bacteria.

While it is possible to generate cosmid libraries, as described above, libraries spanning entire chromosomes are available commercially (Clonetech, South San Francisco, Calif.) or from the Los Alamos National Laboratory. For example, the Los Alamos supplies a library designated LA17NC01 which comprises a set of inserts in cosmids that span the entire chromosome 17 sorted from the mouse-human hybrid cell line, 38L-27. The Los Alamos library for chromosome 20 is designated LA20NC01.

The cosmid probes must be labeled for use in in situ hybridization. The probes may be detectably labeled prior to the hybridization reaction. Alternatively, a detectable label may be selected which binds to the hybridization product. Probes may be labeled with any detectable group for use in practicing the invention. Such detectable group can be any material having a detectable physical or chemical property. Such detectable labels have been well-developed in the field of immunoassays and in general most any label useful in such methods can be applied to the present invention. Thus a label is any composition detectable by spectroscopic, photochemical, biochemical, immunochemical, or chemical means. Useful labels in the present invention include fluorescent dyes, electron-dense reagents, enzymes (as commonly used in an ELISA), biotin, dioxigenin, or haptens and proteins for which antisera or monoclonal antibodies are available. The particular label used is note critical to the present invention, so long as it does not interfere with the in situ hybridization of the probe. In addition the label must be detectible in as low copy number as possible thereby maximizing the sensitivity of the assay and yet be detectible above any background signal. Finally, a label must be chosen that provides a highly localized signal thereby providing a high degree of spatial resolution when physically mapping the probe against the chromosome. In a preferred embodiment, the label is digoxigenin-11-dUTP or biotin-14-dATP, which are then detected using fluorophores.

The labels may be coupled to the probes in a variety of means known to those of skill in the art. In a preferred embodiment the probe will be labeled using nick translation or random primer extension (Rigby, et al. *J. Mol. Biol.,* 113:237 (1977) or Sambrook, et al., Molecular Cloning—A Laboratory Manual, Cold Spring Harbor Laboratory, Cold Spring Harbor, N.Y. (1985)).

Mapping of Probe Library

Once a probe library is constructed, a subset of the probes is physically mapped on the selected chromosome. FISH and digital image analysis can be used to localize cosmids along the desired chromosome. This method is described in detail below and in Lichter et al., *Science*, 247:64–69 (1990). Briefly, the clones are mapped by FISH to metaphase spreads from normal cells using e.g., FITC as the fluorophore. The chromosomes are counterstained by a stain which stains DNA irrespective of base composition (e.g., propidium iodide), to define the outlining of the chromosome. The stained metaphases are imaged in a fluorescence microscope with a polychromatic beam-splitter to avoid color-dependent image shifts. The different color images are acquired with a CCD camera and the digitized images are stored in a computer. A computer program is then used to calculate the chromosome axis, project the two (for single copy sequences) FITC signals perpendicularly onto this axis, and calculate the average fractional length from a defined position, typically the p-telomere.

The accuracy of the mapped positions of the probes can be increased using interphase mapping. Briefly, the distance between two probes which are found by metaphase mapping to be very close in measured in normal interphase nuclei. The genomic distance between the two is equal to the square of the physical distance (Van den Engh et al., *Science* 257:1410 (1992)). If the order is uncertain, the probes are labeled with different colors and their relative distance to a third (distant) probe. Trask et al., *Am. J. Hum. Genet.* 48:1 (1991).

Typically, a mapped library will consist of between about 20 and about 125 clones, more usually between about 30 and about 50 clones. Ideally, the clones are distributed relatively uniformly across the region of interest, usually a whole chromosome.

In situ Hybridization with Mapped Library

The mapped library is then used to screen for chromosomal abnormalities in a sample. In the methods of the invention, a chromosome sample (typically either a metaphase spread or interphase nuclei) is analyzed using standard in situ hybridization techniques. Several guides to the techniques are available, e.g., Gall et al. *Meth. Enzymol.*, 21:470–480 (1981) and Angerer et al. in *Genetic Engineering: Principles and Methods* Setlow and Hollaender, Eds. Vol 7, pgs 43–65 (plenum Press, New York 1985).

Briefly, a chromosomal sample is prepared by depositing cells, either as single cell suspensions or as tissue preparation, on solid supports such as glass slides and fixed by choosing a fixative which provides the best spatial resolution of the cells and the optimal hybridization efficiency.

Generally, in situ hybridization comprises the following major steps: (1) fixation of tissue or biological structure to analyzed; (2) prehybridization treatment of the biological structure to increase accessibility of target DNA, and to reduce nonspecific binding; (3) hybridization of the mixture of nucleic acids to the nucleic acid in the biological structure or tissue; (4) posthybridization washes to remove nucleic acid fragments not bound in the hybridization and (5) detection of the hybridized nucleic acid fragments. The reagent used in each of these steps and their conditions for use vary depending on the particular application.

In some applications it is necessary to block the hybridization capacity of repetitive sequences. In this case, human genomic DNA is used as an agent to block such hybridization. The preferred size range is from about 200 bp to about 1000 bases, more preferably between about 400 to about 800 bp for double stranded, nick translated nucleic acids.

Hybridization protocols for the particular applications disclosed here are described in detail below. Suitable protocols are described in Pinkel et al. *Proc. Natl. Acad. Sci. USA*, 85:9138–9142 (1988) and in EPO Pub. No. 430,402.

Standard in situ hybridization techniques are used to probe a given sample. Hybridization protocols for the particular applications disclosed here are described in detail below. Suitable protocols are described in Pinkel et al. *Proc. Natl. Acad. Sci. USA*, 85:9138–9142 (1988) and in EPO Pub. No. 430,402.

Typically, it is desirable to use dual color FISH, in which two probes are utilized, each labelled by a different fluorescent dye. A test probe that hybridizes to the region of interest is labelled with one dye, and a control probe that hybridizes to a different region is labelled with a second dye. A nucleic acid that hybridizes to a stable portion of the chromosome of interest, such as the centromere region, is often most useful as the control probe. In this way, differences between efficiency of hybridization from sample to sample can be accounted for.

The FISH methods for detecting chromosomal abnormalities can be performed on nanogram quantities of the subject nucleic acids. Paraffin embedded tumor sections can be used, as can fresh or frozen material. Because FISH can be applied to the limited material, touch preparations prepared from uncultured primary tumors can also be used (see, e.g., Kallioniemi, A. et al., *Cytogenet. Cell Genet.* 60:190–193 (1992)). For instance, small biopsy tissue samples from tumors can be used for touch preparations (see, e.g., Kallioniemi, A. et al., *Cytogenet. Cell Genet.* 60:190–193 (1992)). Small numbers of cells obtained from aspiration biopsy or cells in bodily fluids (e.g., blood, urine, sputum and the like) can also be analyzed. For prenatal diagnosis, appropriate samples will include amniotic fluid and the like.

Once a region of interest has been identified and mapped with the methods of the invention, one of skill will recognize that there are numerous means of identifying and/or screening for this region. The region may be sequenced by digesting chromosomal DNA with restriction enzymes and identifying the specific duplication-bearing fragments using the mapped cosmids of the invention as hybridization probes. The positive clones may then be subcloned into appropriate vectors and sequenced.

Sequence information permits the design of highly specific hybridization probes or amplification primers suitable for detection of the target sequences. This is useful for diagnostic screening systems as well as research purposes.

Means for detecting specific DNA sequences are well known to those of skill in the art. For instance, oligonucleotide probes chosen to be complementary to a select subsequence with the region can be used. Alternatively, sequences or subsequences may be amplified by a variety of DNA amplification techniques (for example via polymerase chain reaction, ligase chain reaction, transcription amplification, etc.) prior to detection using a probe. Amplification of DNA increases sensitivity of the assay by providing more copies of possible target subsequences. In addition, by using labeled primers in the amplification process, the DNA sequences may be labeled as they are amplified.

The following example is provided to illustrate but not limit the present invention.

EXAMPLE 1

Mapping of Chromosome 20

Results of experiments employing "Comparative Genome Hybridization " (CGH) to screen the whole genome for amplifications, indicate that sequences on chromosome 20 q are frequently amplified in both breast tumor cell lines and primary breast tumors. In order to define these genetic alterations in more detail, a library of cosmid FISH probes was isolated and physically mapped to chromosome 20. The library of mapped probes could then be used to probe chromosome 20 using FISH to determine the particular loci involved in amplifications and deletions. This example details the creation of the library of probes physically mapped to chromosome 20.

Cosmids from a chromosome 20 library were isolated at random from single bacterial clones using Qiagen columns according to the manufacturers instructions (Qiagen Inc., Chatsworth, Calif.). Cosmid DNA was labeled by nick-translation with biotin-14-dATP (Gibco), to give fragments of length 0.3–1.0 kb (under non-denaturing conditions). These probes were hybridized to normal human lymphocyte metaphase preparations. The slides were denatured at 70° C for 3 minutes in 70% formamide/2× SSC, followed by dehydration in 70%/85%/100% ethanol. The slides were hybridized overnight with 40 ng of human biotin-labeled cosmid DNA in the presence of 5 µg human placental DNA (Sigma) in 10 µl 50% formamide/2× SSC at 37° C. The probe was denatured at 70° C. for 5 minutes and allowed to temperature at 37° C. prior to application to the slides. The slides were washed three times in 50% formamide/2× SSC, once in 0.1× SSC, and twice in 2× SSC at 45° C. (15 minutes for each wash). The remaining steps were performed at room temperature.

The slides were equilibrated in 4× SSC/0.1% Triton X100 ("wash " buffer), and blocked for 5 minutes in wash buffer with 5% dry milk/0.1% Sodium Azide ("block " buffer). Staining for biotinylated probe was done with 5 µg/ml avidin-FITC (60 minutes, in block buffer), amplified by 30 minutes incubation with 5 µg/ml biotinylated anti-avidin (in block buffer), and another 30 minutes incubation with avidin-FITC. The slides were then washed three times for 10 minutes each after each staining step. The slides were equilibrated in 0.1× SSC prior to application of anti-fade solution (ref) with 0.05 µg/ml propidium iodide and 0.4 µM DAPI.

The slides were first inspected in a fluorescence microscope to determine whether signals were present (29/40 cosmids tested) and, if so, whether the cosmid detected single-copy sequences (28/40 cosmids tested). One cosmid hybridized to the centromere of chromosome 20, but also hybridized to the p-arms of acrocentric chromosomes. Metaphases hybridized with cosmids detecting single copy sequences were analyzed in a Nikon SA fluorescence microscope equipped with a CCD camera (Photometrics Inc., Tucson, Ariz.) and a polychromatic beamsplitter (Chroma Technology Inc., Brattleborrough, Vt.) to avoid color-dependent image shifts. The images of chromosome 20 were analyzed with computer software to determine the mean position (of the two FITC probe spots) in term of fractional length from the p telomere (FLpter) along the chromosome axis as defined by propidium iodide staining using the methods generally described by Lichter et al., supra.

Several metaphases were analyzed for each cosmid, the FLpter value and the SEM are given in Table 1. The average SD of all the FLpter values was 0.030, corresponding to ~2Mb. Cosmids which are separated by a FLpter value of less than 2.5 times the SEM could not be ordered with statistical confidence. The vertical lines in Table 1 span cosmids which could not be ordered reliably.

TABLE 1

FLpter values of chromosome 20 cosmids.

| Cosmid | FLpter | n | SEM | |
|---|---|---|---|---|
| cS20.10F3: | 0.040 | 8 | 0.010 | * |
| cS20.10E3: | 0.048 | 9 | 0.011 | |
| cS20.10G1: | 0.074 | 15 | 0.006 | |
| cS20.10F5: | 0.125 | 12 | 0.008 | |
| cS20.10H5: | 0.155 | 8 | 0.008 | |
| cS20.10D3: | 0.191 | 8 | 0.010 | |
| cS20.10F1: | 0.213 | 6 | 0.010 | |
| cS20.10D4: | 0.258 | 7 | 0.017 | |
| cS20.10G5: | 0.332 | 9 | 0.012 | |
| cS20.10D2: | 0.503 | 8 | 0.012 | |
| cS20.10G2: | 0.507 | 7 | 0.015 | |
| cS20.10B3: | 0.563 | 13 | 0.008 | | |
| cS20.10C1: | 0.582 | 14 | 0.008 | | |
| cS20.10C2: | 0.594 | 10 | 0.008 | | |
| cS20.10D1: | 0.600 | 8 | 0.011 | | |
| cS20.10G3: | 0.608 | 5 | 0.009 | |
| cS20.10A4: | 0.610 | 5 | 0.017 | |
| cS20.10H4: | 0.612 | 7 | 0.011 | | |
| cS20.10B4: | 0.664 | 10 | 0.014 | |
| cS20.10B1: | 0.700 | 14 | 0.006 | |
| cS20.10E4: | 0.713 | 11 | 0.007 | | |
| cS20.10C5: | 0.728 | 7 | 0.016 | | | |
| cS20.10B5: | 0.740 | 9 | 0.009 | | |
| cS20.10A1: | 0.757 | 14 | 0.007 | |
| cS20.10H1: | 0.802 | 13 | 0.008 | |
| cS20.10E2: | 0.846 | 12 | 0.009 | |
| cS20.10G4: | 0.905 | 15 | 0.011 | |
| cS20.10D5: | 0.906 | 13 | 0.006 | |

*Any two cosmids connected by a vertical line cannot be ordered with statistical confidence.

Figure 1:
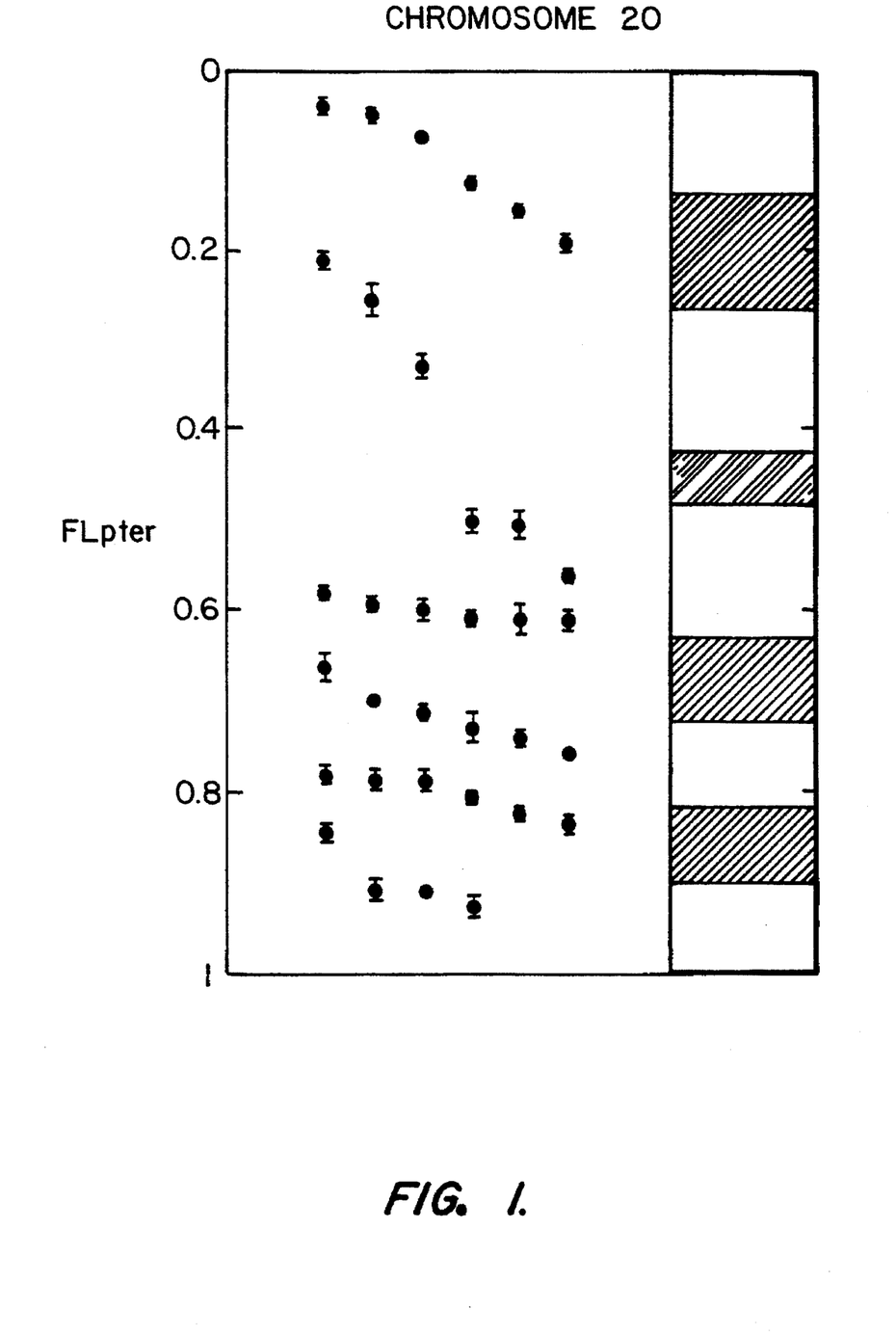
FIG. 1 shows the physical location of chromosome 20 specific cosmids. The locations, determined by metaphase Fish and digital image analysis, are shown as the mean of the Flpter (±sem).

The FLpter values are graphically illustrated in FIG. 1, together with an ideogram of chromosome 20. A chromosome 20 centromere probe (p3-4) mapped to FLpter=0.443 (SEM=0.008, n=10), in good agreement with the position of the centromere in this ideogram and the reported physical location of the chromosome 20 centromere (Schnittger, et al. *Genomics*, 16:50–55 (1993); Passarge, E. pp. 135–205 In *Methods in Human Genetics* Schwarzacher & Wolf, Eds. Springer, Berlin (1974). The corresponding band locations indicated in FIG. 1 were also confirmed visually relative to the position of DAPI bright bands (corresponding approximately to Giemsa-stained bands under these conditions). The cosmids seem to be fairly evenly distributed over the whole chromosome, with possible under- and over-representation in the centromere region and the region with a FLpter value of –0.6, respectively.

Mapping Chromosome 17

The chromosome 17 cosmid library (designated LA17NC01) was prepared at the Los Alamos National Laboratory from chromosomes flow sorted from the mouse-human hybrid cell line, 38L-27. The sorted chromosomes were examined for purity using FISH. DNA was extracted, partially digested with Sau3A1, dephosphorylated, and cloned into sCos1 with HB101 as the host. Characterization of the initial library showed it to have 39× representation with 92% human inserts, 2.6% mouse and 5.4% non-recombinant.

Approximately 12,000 colonies were picked and grown in microtiter plates to provide a 5× coverage of chromosome 17. The contents of one set of these plates were pooled together to provide a pooled 5× library. For this study, the 5× library was plated and 288 individual clones were picked at random and arrayed in three microtiter plates. Seventy one of these were analyzed using FISH. Twenty cosmid probes previously mapped by genetic linkage analysis (O'Connell, et al. *Genomics*, 15:38–47 (1993) also were selected for analysis.

FISH was performed essentially as described previously. See Kallioniemi, et al. *Proc. Natl. Acad. Sci. USA*, 89:5321–5325 (1992) and Pinkel, et al., *Proc. Natl. Acad. Sci. USA*, 85:9138–9142 (1988) both of which are incorporated herein by reference. Briefly, DNA was isolated from individual clones and from the 5× pool using Qiagen columns (Qiagen Inc. Chatsworth, Calif.) according to the manufacturers instructions. DNA was labeled using nick translation with biotin-14-dATP. DNA from a chromosome 17 centromeric repeat probe was labeled with digoxigenin-11-dUTP. Each probe was hybridized along with the chromosome 17 centromere probe to metaphase spreads prepared from normal peripheral blood lymphocytes. Hybridized probes were detected using Avidin-Texas Red and anti-digoxigenin-FITC. Metaphase chromosomes were counterstained using DAPI in an anti-fade solution.

Analysis of the samples was accomplished using a digital image analysis system as described above. A semi-automated program was used to 1) segment each DAPI image, 2) define the chromosome medial axis, 3) define the center of mass of each candidate hybridization domain, and 4) calculate the fractional location of each domain along the chromosome axis relative to the telomere of the short arm of the chromosome (FLpter). Candidate hybridization domains defined by the analysis program were confirmed by visual inspection. A chromosome 17 centromeric probe was used in each hybridization as an internal reference. If the FLpter value of the centromere did not fall within the expected range (0.300<FLpter<0.342), the chromosome was not used for FLpter calculation.

FISH using DNA from the whole library (LA17NC01) as a painting probe resulted in intense, specific staining of the entire chromosome 17 indicating that all portions of the chromosome are represented in the library. Seventy-one individual cosmids selected from the library were roughly mapped using FISH. Of these, 15 (21%) mapped to the p-arm, 46 (65%) to the q-arm, 2 (3%) to the peri-centromeric repeat region. This distribution is approximately that expected for randomly distributed probes. Eight cosmids (11%) gave no signal on any human chromosome and so may have been of non-human origin. This is consistent with the initial library characterization by slot blot analysis that showed 8% of the clones to be non recombinant or to contain a mouse insert.

In order to identify probes that would be useful for FISH analysis of interphase cells, the 40 cosmids that gave the most distinctive hybridization signals both in metaphase and interphase were mapped using digital image analysis. FLpter values are listed in Table 2 for each cosmid. The standard deviation (sd) for the FLpter measurements and the number of chromosomes analyzed for each probe (n) are listed to permit calculation of the standard error of the mean (sem=$\sqrt{sd/n}$) for each FLpter estimate. Probes whose FLpter means differ by >2.5 sem can be ordered with statistical confidence.

Figure 3:
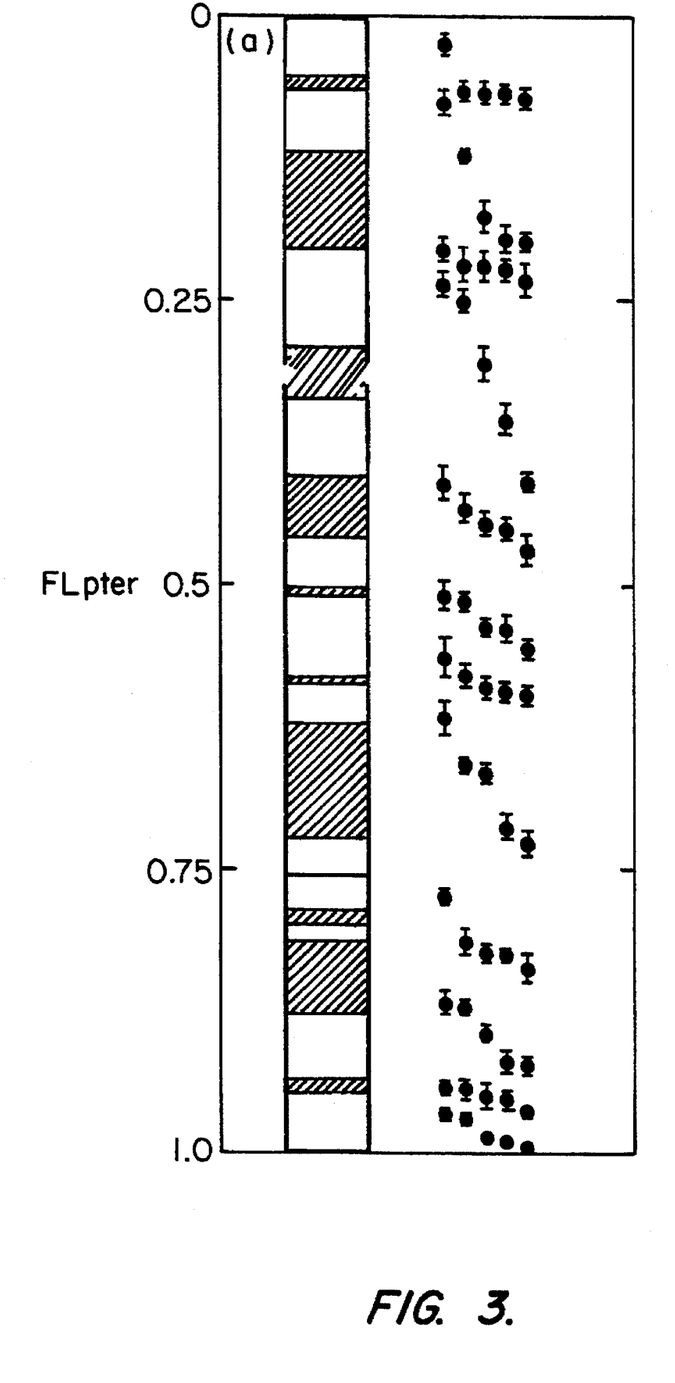
FIG. 3 shows the physical locations on chromosome 17 of 40 cosmids selected from the library LA17NC01. The locations, determined by metaphase FISH and digital image analysis, are shown as the mean of the FLpter (±sem).

FIG. 3 shows that the probes are distributed over the whole chromosome, although there seems to be a slight over-representation of sequences near 17p11-p12. Two color, pair-wise hybridizations to metaphase chromosomes showed that these did not represent the same clone. FLpter values are related to the ICSN chromosome 17 ideogram in FIG. 3 since other studies have shown a reasonable correspondence between FLpter value and band location (Lawrence, et al., *Science*, 249:928–932 (1990); Lichter, P., et al. *Science* 247:64–69. (1990)). However, this relation should be considered only approximate since band locations on the ideograms are inexact.

Twenty cosmids that had also been mapped by genetic linkage analysis (O'Connell, et al. *Genomics*, 15: 38–47 (1993)) were also physically mapped. The average standard deviation of the FLpter measurements for all cosmids was 0.035. This corresponds to about 3 Mbs. The average mapping precision determined as the standard error of the mean (sem) was about 0.01 corresponding to ~1 Mb. Cosmids separated by ~2.5 Mb (i.e. whose means are separated by >2.5 sem in Table 2) can be ordered with statistical confidence.

Detection of Amplifications in Chromosome 20

Figure 2:
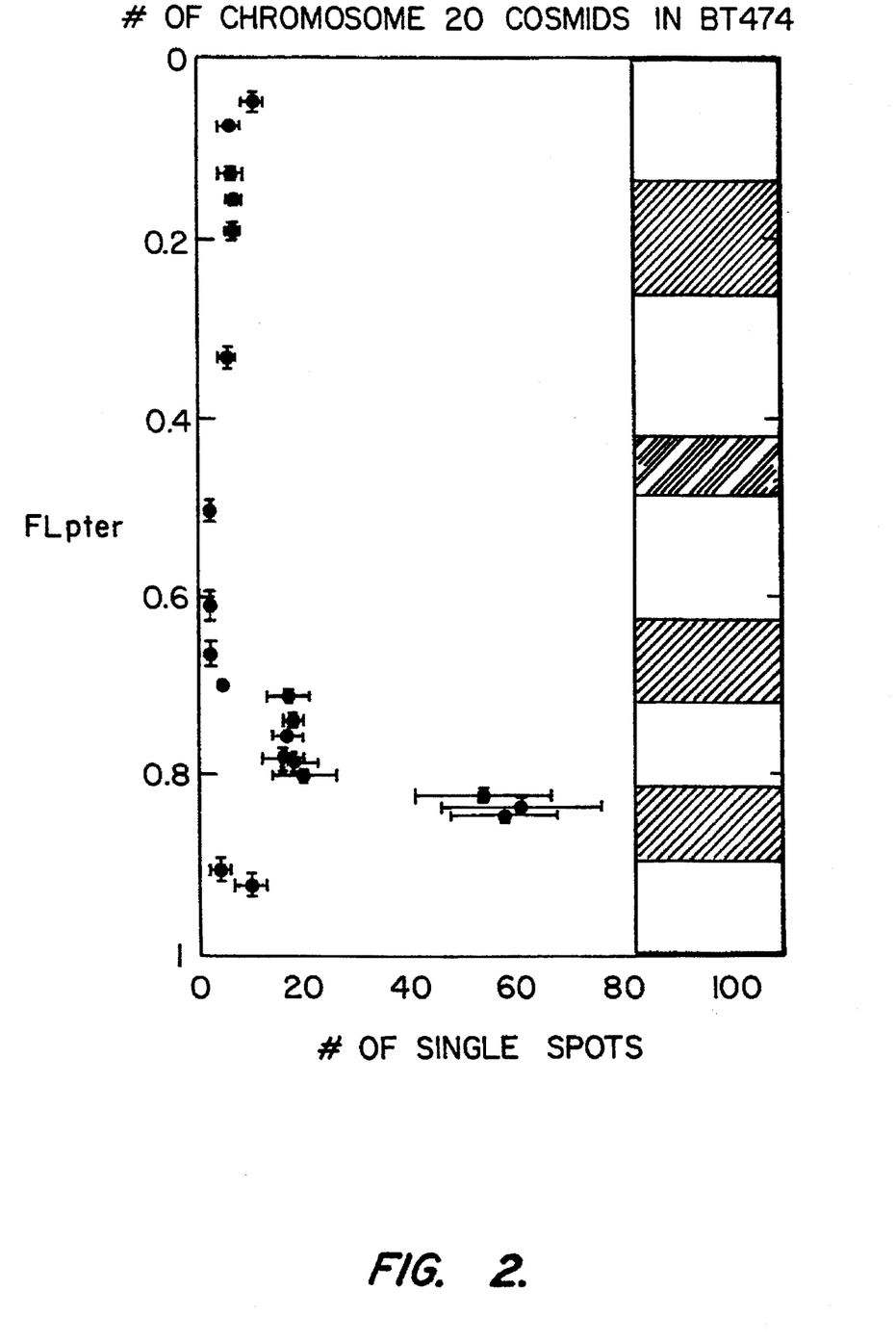
FIG. 2 shows the spot numbers of the different mapped, chromosome 20-specific cosmids (see FIG. 1) counted in interphase BT474 breast cancer cells. A region around FLpter-0.85 is heavily amplified. This region is therefore likely to contain a (proto)-oncogene.

FIG. 2, shows an example where the spot numbers of the different mapped, chromosome 20-specific cosmids (see FIG. 1) were counted in interphase BT474 breast cancer cells using standard FISH techniques as described above. A region around FLpter-0.85 is heavily amplified.

All of the references cited herein are hereby incorporated by reference. For the purposes of clarity and understanding, the invention has been described in these examples and the above disclosure in some detail. It will be apparent, however, that certain changes and modifications may be practiced within the scope of the appended claims.

TABLE 2

FLpter values measured for 60 cosmids including 20 that were mapped previously by genetic linkage analysis (shown in bold type).

| Probe | FLpter | sd | n | Gen loc(cM) |
| --- | --- | --- | --- | --- |
| cK17.79 | 0.025 | 0.018 | 5 | |
| cLS17.6 | 0.066 | 0.037 | 25 | 13 |
| fLB17.8 | 0.068 | 0.037 | 16 | 15 |
| cK17.29 | 0.068 | 0.031 | 17 | |
| fLB17.9 | 0.073 | 0.037 | 20 | 19 |
| fLB17.16 | 0.076 | 0.041 | 28 | 15–18* |
| cK17.22 | 0.122 | 0.020 | 11 | |
| cK17.88 | 0.177 | 0.042 | 9 | |
| cK17.31 | 0.197 | 0.036 | 10 | |
| cK17.24 | 0.199 | 0.028 | 11 | |
| cK17.80 | 0.205 | 0.035 | 11 | |
| cK17.17 | 0.219 | 0.044 | 8 | |
| cK17.83 | 0.220 | 0.043 | 10 | |
| cK17.19 | 0.224 | 0.031 | 10 | |
| pYNM67 | 0.233 | 0.057 | 15 | 59–63* |
| cK17.81 | 0.236 | 0.037 | 11 | |
| fLB17.5 | 0.251 | 0.040 | 17 | 61–64 |
| cK17.23 | 0.306 | 0.029 | 4 | |
| cK17.75 | 0.355 | 0.038 | 9 | |
| fLB17.18 | 0.410 | 0.035 | 20 | 77 |
| cK17.37 | 0.411 | 0.033 | 5 | |
| cK17.18 | 0.433 | 0.044 | 12 | |
| cK17.32 | 0.446 | 0.030 | 9 | |
| fLB17.6 | 0.451 | 0.040 | 18 | 77–80* |
| cK17.89 | 0.470 | 0.048 | 12 | |
| cK17.86 | 0.510 | 0.035 | 8 | |
| cK17.25 | 0.515 | 0.023 | 8 | |
| cK17.38 | 0.537 | 0.031 | 14 | |
| cK17.74 | 0.539 | 0.036 | 9 | |
| fLB17.1 | 0.557 | 0.038 | 19 | 88 |
| cK17.16 | 0.564 | 0.048 | 8 | |
| fLB17.20 | 0.580 | 0.046 | 21 | 90 |
| cK17.11 | 0.591 | 0.035 | 12 | |
| cLS17.13 | 0.594 | 0.040 | 22 | 90 |
| cK17.87 | 0.598 | 0.026 | 8 | |
| cK17.30 | 0.618 | 0.041 | 9 | |
| cK17.76 | 0.657 | 0.019 | 12 | |
| cK17.84 | 0.666 | 0.024 | 9 | |
| cK17.73 | 0.714 | 0.037 | 11 | |
| cK17.33 | 0.728 | 0.039 | 13 | |
| fLB17.4 | 0.773 | 0.033 | 20 | 111–123* |
| cK17.72 | 0.814 | 0.037 | 11 | |
| cK17.14 | 0.823 | 0.026 | 11 | |
| fLB17.14 | 0.825 | 0.033 | 25 | 120 |

TABLE 2-continued

FLpter values measured for 60 cosmids including 20 that were mapped previously by genetic linkage analysis (shown in bold type).

| Probe | FLpter | sd | n | Gen loc(cM) |
|---|---|---|---|---|
| cK17.28 | 0.837 | 0.052 | 16 | |
| cK17.53 | 0.867 | 0.039 | 15 | |
| cK17.12 | 0.871 | 0.023 | 12 | |
| cK17.54 | 0.894 | 0.032 | 16 | |
| cK17.15 | 0.919 | 0.035 | 12 | |
| c1–26 | 0.922 | 0.035 | 18 | 144 |
| fLB17.17 | 0.942 | 0.037 | 25 | 148–151* |
| cK17.27 | 0.943 | 0.032 | 13 | |
| cEFD52 | 0.950 | 0.045 | 15 | 167 |
| cK17.71 | 0.953 | 0.028 | 11 | |
| cLS17.9 | 0.962 | 0.027 | 21 | 159 |
| fLB17.7 | 0.964 | 0.026 | 24 | 165–169* |
| fLB17.2 | 0.969 | 0.030 | 28 | 166–170* |
| fLB17.10 | 0.985 | 0.016 | 23 | 177 |
| cK17.77 | 0.989 | 0.015 | 9 | |
| cK17.78 | 0.994 | 0.005 | 12 | |

*Genetic locations for these probes were estimated graphically from information presented by 'Connell, et al. Genomics, 15: 38–47 (1993).

What is claimed is:

1. A kit for the detection of an amplification at about position FLpter 0.85 on human chromosome 20, the kit comprising a compartment which contains a composition consisting essentially of one or more nucleic acid probes, each of which binds selectively to a target polynucleotide sequence at about FLpter 0.85 on human chromosome 20.

2. The kit of claim 1, wherein the probe is labeled.

3. The kit of claim 2, wherein the label is selected from the group consisting of digoxigenin and biotin.

4. The kit of claim 2, wherein the probe binds selectively to a target polynucleotide sequence from about Flpter 0.740 to about Flpter 0.846.

5. The kit of claim 1, further comprising a second compartment comprising a composition consisting essentially of one or more probes, each of which binds selectively to a sequence in the centromere of chromosome 20.

6. The kit of claim 1, further comprising Texas red avidin and biotin-labeled goat anti-avidin antibodies.

7. A composition consisting essentially of one or more nucleic acid probes, each of which binds selectively to a target polynucleotide sequence at about FLpter 0.85 on human chromosome 20.

8. The composition of claim 7, wherein the probe is labeled.

9. The composition of claim 8, wherein the label is selected from the group consisting of digoxigenin and biotin.

10. The composition of claim 7, wherein the probe binds selectively to a target polynucleotide sequence from about Flpter 0.740 to about Flpter 0.846.

11. The composition of claim 7, further comprising a reference probe which binds selectively to a sequence in the centromere of chromosome 20.

* * * * *

UNITED STATES PATENT AND TRADEMARK OFFICE
CERTIFICATE OF CORRECTION

PATENT NO. : 5,633,365

DATED : March 27, 1997

INVENTOR(S) : STOKKE et al.

It is certified that error appears in the above-indentified patent and that said Letters Patent is hereby corrected as shown below:

In column 1 at line 6, insert the following statement:
 --This invention was made with Government support under Grant No. CA45919, awarded by the National Institutes of Health. The Government has certain rights in this invention.--

Signed and Sealed this

Twenty-sixth Day of October, 1999

*Attest:*

Q. TODD DICKINSON

*Attesting Officer*   *Acting Commissioner of Patents and Trademarks*